United States Patent [19]

Marangos

[11] Patent Number: 5,373,021

[45] Date of Patent: Dec. 13, 1994

[54] USE OF DISULFIRAM FOR NEURONAL PROTECTION

[75] Inventor: Paul J. Marangos, Encinitas, Calif.

[73] Assignee: Cypros Pharmaceutical Corporation, Carlsbad, Calif.

[21] Appl. No.: 52,775

[22] Filed: Apr. 26, 1993

Related U.S. Application Data

[63] Continuation-in-part of Ser. No. 787,062, Nov. 4, 1991, Pat. No. 5,206,264.

[51] Int. Cl.$^5$ .................. A61K 31/27; A61K 31/16; A61K 31/105
[52] U.S. Cl. .................. 514/483; 514/599; 514/707; 514/921
[58] Field of Search .............. 514/483, 289, 777, 778, 514/599, 58, 707, 921

[56] References Cited

U.S. PATENT DOCUMENTS

| | | | |
|---|---|---|---|
| 4,678,809 | 7/1987 | Phillips | 514/599 |
| 4,888,347 | 12/1989 | Woodruff et al. | 514/289 |
| 5,024,998 | 6/1991 | Bodor | 514/58 |

*Primary Examiner*—Marianne M. Cintins
*Assistant Examiner*—K. Weddington
*Attorney, Agent, or Firm*—Patrick D. Kelly

[57] ABSTRACT

This invention discloses a rapid-diffusion injectable formulation, comprising disulfiram or a suitable salt or analog of disulfiram. Unlike slow-release injectable formulations designed to ensure that chronic alcoholics have significant quantities of disulfiram in their blood at all time, the rapid-diffusion injectable formulation disclosed herein is designed to reduce the hypoxic or ischemic damage caused by crisis events such as stroke, heart attack, cardiac arrest, or asphyxiation. A rapid-diffusion injectable formulation can contain disulfiram mixed with water, an organic compound having a plurality of hydroxyl groups (such as pharmaceutically acceptable glycols or polysaccharides; propylene glycol, dextrans, and cyclodextrins are often used for such purposes), and a buffer. When a rapid-release formulation is injected during or immediately after a hypoxic-/ischemic crisis or before a patient is subjected to controlled cardiac arrest or bypass during surgery, it can suppress damage by oxygenated free radicals, it can chelate copper and iron which would otherwise promote lipid peroxidation of cell membranes, and it can generate metabolites such as tryptophol that can suppress metabolic activity and demands in neurons and affected tissue.

9 Claims, No Drawings

USE OF DISULFIRAM FOR NEURONAL PROTECTION

RELATED APPLICATION

This application is a continuation-in-part of U.S. application Ser. No. 07/787,062, filed on Nov. 4, 1991, which issued as U.S. Pat. No. 5,206,264 on Apr. 27, 1993.

BACKGROUND OF THE INVENTION

This invention is in the field of drugs, pharmacology, and neurology. It relates to drugs that can protect the nervous and cardiovascular systems against conditions such as ischemia and hypoxia.

Ischemia refers to a condition of inadequate blood supply to an internal organ or portion of an organ. This condition is encountered during events such as stroke, heart attack, cardiac arrest, injury or trauma, shock, and internal hemorrhaging due to rupture of an aneurysm. Hypoxia refers to a state of inadequate oxygen supply to an organ. Hypoxia is a broader term and, as used herein, covers all forms of ischemia, since ischemia (inadequate blood flow) will lead directly to a hypoxia (an oxygen deficit) in any affected organ. Hypoxia can also occur despite normal blood flow, in conditions such as anemia, carbon monoxide poisoning, or asphyxia (which is used herein to include drowning, suffocation, perinatal asphyxia, etc).

Ischemia and hypoxia can lead to severe and permanent damage to the brain and central nervous system (CNS), even when they last only a few minutes. They are often fatal, and even when not, they can lead to widespread cell death in the central nervous system (CNS) causing crippling and irreversible damage such as paralysis, loss of speech or memory, and other effects that are physically, emotionally, and financially devastating.

In addition, "peripheral" hypoxia and/or ischemia can occur outside the CNS, in internal organs which are served by the sympathetic and parasympathetic nervous systems, and in tissue where blood flow is blocked or hindered by processes such as phlebitis, blood clots', shock, or loss of blood due to injury or hemorrhage.

Hypoxic/ischemic damage does not stop during "reperfusion," when oxygen or blood flow are restored to an organ or region of the brain; instead, the damage often increases sharply when oxygen is reintroduced after an anoxic period. During anoxia, certain metabolites and enzymes can accumulate which, when the anoxia ends, convert oxygen into a highly reactive free radical known as superoxide ($O_2^-$). Superoxide can attack any molecule, and it also promotes the release of iron ions from ferritin, which in turn promotes a process called "lipid peroxidation" which destroys cell membranes, as discussed in more detail below.

For more information on the cellular and molecular mechanisms involved in damage caused by hypoxia and/or ischemia, and on the various pharmaceutical approaches that are being studied in the hope of developing effective treatments for stroke, cardiac arrest, and other hypoxic or ischemic events, see Krause et al 1988. For additional background information on the structure, functioning, and biochemistry of the central and peripheral nervous systems, see Adelman 1987.

Disulfiram

Disulfiram is a common name for tetraethylthiuram disulfide. The chemical structure is as follows:

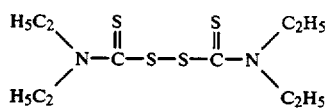

By itself, disulfiram is relatively nontoxic; most people are completely unaffected by disulfiram when it is administered alone. However, when disulfiram is administered in conjunction with ethyl alcohol (the form of alcohol found in intoxicating beverages), it causes severe adverse reactions, including severe headaches, nausea, vomiting, sweating, thirst, weakness, and low blood pressure. Therefore, it is widely used under the trademark "Antabuse" to help treat chronic alcoholism. After an alcoholic swallows a tablet of disulfiram, it persists in the blood for several days, and the alcoholic knows that if he or she drinks alcohol during those days, he or she will become severely ill. This helps alcoholics increase their resolve not to drink alcohol.

On a molecular level, disulfiram is believed to perform this function primarily by blocking the metabolism of acetaldehyde. When people drink alcohol, acetaldehyde is formed as a product of alcohol metabolism in the body. Acetaldehyde is toxic and causes symptoms which can become severe if the acetaldehyde accumulates to significant concentrations. In most people, this doesn't occur, since acetaldehyde is quickly converted into other compounds by enzymes such as aldehyde dehydrogenase (ALDH). However, in alcoholics who are treated with disulfiram, the disulfiram blocks the activity of the ALDH enzyme. This causes acetaldehyde to accumulate to levels that cause severe adverse effects.

Disulfiram also causes various other effects, some of which are difficult to precisely identify and quantify. For example, direct injection of acetaldehyde into animals usually causes an increase in blood pressure; however, administration of disulfiram in conjunction with alcohol causes a drop in blood pressure, for reasons that are not entirely understood. It is suspected that disulfiram might deactivate dopamine-beta-hydroxylase (DBH), an enzyme that is involved in the synthesis of epinephrine (adrenalin) in sympathetic nerve terminals.

Disulfiram also is known to form chemical complexes with certain metal ions, especially copper and iron. This chelating effect makes the metal ions unavailable for other metabolic functions. Since a wide variety of enzymes and other proteins require metal ions for activity, this can cause various effects that are difficult to quantify and can vary between different individuals.

In addition, U.S. Pat. Nos. 4,870,101 and 5,011,857 (Ku et al, 1989 and 1991) indicate that disulfiram and certain other anti-oxidants can suppress the release of interleukin-1, a natural hormone that can aggravate inflammation in various conditions such as rheumatoid arthritis and psoriasis.

Although disulfiram is normally administered in oral form (usually 250 mg tablets or capsules), U.S. Pat. No. 4,687,809 (Phillips 1987) describes an injectable formulation. This formulation is a slow-release formulation, and its sole purpose is to sustain moderately high concentrations of disulfiram in the bloodstream for prolonged periods of time (weeks or months). By mixing disulfiram with a biodegradable polymer, or by forming a slurry of disulfiram (which is very insoluble in water) in aqueous saline solution, substantial concentrations of disulfiram in blood serum can be maintained for periods up to about 90 days. The use of this slow-release injectable formulation is to treat alcoholics who are unable to maintain disulfiram therapy on their own, which normally requires taking a disulfiram capsule each day. If an alcoholic is unable to resist the temptation to avoid taking the daily capsules, then injection of a slow-release formulation on a timed basis (such as once a month) can overcome that failure or refusal, and provide effective treatment for chronic alcoholics who would otherwise not be adequately helped.

For more information on the chemistry and clinical use of disulfiram, see Banys 1988 (a review article) and the various articles cited therein.

There have been two reports indicating that disulfiram can have certain types of cytoprotective effects. Jennische and Hansson 1984 stated that disulfiram helped protect against post-ischemic cell death in liver cells, and Misiorowski et al 1983 stated that disulfiram can help protect against lipid peroxidation in cell homogenates obtained by grinding up spinal cord tissue obtained from dogs. Despite those reports, there apparently has been no effort during the intervening decade to develop disulfiram into a neuroprotective drug. In addition, since various experimental limitations and caveats were set forth in the Misiorowski et al report, it is accurate to state that, to the best of the Applicant's knowledge, no prior publications have ever stated or even suggested that disulfiram can reduce hypoxic and/or ischemic damage in the central nervous system. Similarly, the Applicant is not aware of any prior publications which suggest that disulfiram could or would be useful to prevent the damage caused by progressive neurodegenerative diseases, such as Alzheimer's, disease, Parkinson's disease, Huntington's disease, or amyotrophic lateral sclerosis.

Accordingly, one object of this invention is to disclose a rapid-diffusion injectable formulation containing disulfiram, for use in reducing the hypoxic damage caused by crisis events such as stroke, heart attack, cardiac arrest, or asphyxiation.

Another object of this invention is to disclose that disulfiram can be useful in reducing hypoxic damage to the brain in patients suffering from stroke, cardiac arrest, and other conditions that generate hypoxia and/or ischemia inside the brain.

Another object of this invention is to provide an effective treatment to minimize neurologic damage caused by hypoxia and/or ischemia, using a drug that has already been extensively tested and widely used, which has few adverse side effects.

A fourth object of this invention is to disclose a treatment that can help reduce some of the oxidative, excitotoxic, and other damaging processes that are involved in some neurodegenerative diseases.

SUMMARY OF THE INVENTION

This invention discloses a rapid-diffusion injectable formulation, comprising disulfiram or a suitable salt or analog of disulfiram. Unlike slow-release injectable formulations designed to ensure that chronic alcoholics have significant quantities of disulfiram in their blood at all time, the rapid-diffusion injectable formulation disclosed herein is designed to reduce the hypoxic or ischemic damage that is caused by crisis events such as stroke, heart attack, cardiac arrest, or asphyxiation. The injectable formulation can contain disulfiram mixed with water, an organic compound having a plurality of hydroxyl groups (propylene glycol, dextran compounds, and cyclodextrin compounds are often used for such purposes), and a buffer compound. When a rapid-release formulation is injected during or immediately after a hypoxic/ischemic crisis or before a patient is subjected to controlled cardiac arrest or bypass during surgery, it can inhibit enzymes such as xanthine oxidase which would otherwise generate oxygenated free radicals, which are highly reactive chemical compounds that non-specifically attack and damage essential molecules and cells; it can chelate copper and iron, thereby suppressing lipid peroxidation and protecting cell membranes from destruction; and it can generate metabolites such as tryptophol, which can reduce metabolic activity and demands in neurons and affected tissue, which can be useful during cytotoxic events.

DESCRIPTION OF THE PREFERRED EMBODIMENTS

This invention relates to a rapid-diffusion injectable formulation comprising disulfiram or a suitable salt or analog of disulfiram. Unlike slow-release injectable formulations designed to ensure that chronic alcoholics have significant quantities of disulfiram in their blood at all time, the rapid-diffusion injectable formulation disclosed herein is designed to reduce the hypoxic or ischemic damage that is caused by crisis events such as stroke, heart attack, cardiac arrest, or asphyxiation, or during controlled cardiac arrest or bypass during surgery. The injectable formulation can contain disulfiram mixed with water, an organic compound having a plurality of hydroxyl groups (such as a pharmaceutically acceptable glycol or polysaccharide molecule, such as propylene glycol, dextran, or cyclodextrin), and a buffer compound (such as a mixture of a carboxylic acid and a salt thereof).

Two useful effects of disulfiram, when it is used to reduce or prevent cytotoxic damage, involve (a) suppressing the formation of oxygenated free radicals, and (b) capturing (i.e., trapping and sequestering, reacting with, or otherwise removing) free radicals that have already been formed. In chemical terminology, a free radical is an atom or molecule with an unpaired electron. Except in certain very limited situations that are not relevant here, oxygen-containing free radicals are extremely reactive, and they will non-specifically attack nearly any type of molecule they encounter inside the body.

One of the most important enzymes involved in the generation of oxidative free radicals under ischemic conditions is xanthine oxidase. This enzyme usually exists in a form known as the "D" form, which is often called xanthine dehydrogenase. The D form is involved in the degradation of adenosine triphosphate through two intermediate metabolites (hypoxanthine and xanthine) into uric acid, which is secreted and eliminated from the body in urine. The metabolic steps involving xanthine dehydrogenase generate water as a byproduct.

However, under ischemic conditions, the D form of xanthine dehydrogenase is converted into a different form known as xanthine oxidase (also known as the "O" form) which generates highly reactive superoxide ($O_2^-$) free radicals (instead of water) as the byproduct when adenosine is degraded into uric acid. The superoxide radicals created by xanthine oxidase cause major damage to ischemic or hypoxic cells and tissue. By inhibiting the activity of xanthine oxidase (and possibly other oxidative enzymes as well), disulfiram can suppress the formation of oxygenated free radicals. Furthermore, disulfiram, being a disulfide in its low oxidation state, can capture oxygenated free radicals that have already been generated. This will reduce the amount of damage caused by the oxidative free radicals.

A second benefit that can arise when disulfiram is used as a cytoprotective agent involves the chelation of copper and iron. Iron ions are normally coupled to various proteins such as ferritin (a storage protein) and transferring (a transport protein). When superoxide is present (which can occur under ischemic conditions, as discussed above), ferric ions ($Fe^{3+}$) stored inside ferritin are converted into ferrous ions ($Fe^{2+}$), which are released from the ferritin. These ions can catalyze a process called lipid peroxidation, a complex process involving lipid hydroperoxides and lipid peroxyl free radicals. In this process, lipids (which are the partly polar, partly non-polar molecules that form cell membranes) are attacked, and the double bonds in the fatty acid side chains are altered, which destroys the ability of the lipids to function as the structural components of cell membranes. Lipid peroxidation is a chain reaction; the molecules that destroy lipids are not inactivated or bound up by the reaction, so a single such molecule can destroy thousands of lipid molecules until something stops the process.

Transition metals such as iron or copper can act as catalysts for lipid peroxidation; the peroxidation process does not occur in the absence of transition metals, and it can be inhibited by agents which chelate (i.e., which chemically tie up and inactivate) transition metals. Therefore, in mammals that are treated with disulfiram as a cytoprotective agent, the disulfiram, which chelates and thereby inactivates iron and copper, will suppress lipid peroxidation and reduce lipid peroxidation damage to cell membranes.

In addition to these beneficial effects, disulfiram may also have various other beneficial effects when used to treat hypoxia/ischemia. For example, when administered to mammals, disulfiram induces the biosynthesis of a compound known as tryptophol (also called 3-indole ethanol). This compound reduces the rate of glucose utilization and other metabolic activity in neurons, and can reduce body temperature (Cornford et al 1981). When treating someone suffering from hypoxia or ischemia, the suppression of metabolic activity and temperature can be very useful, since it can delay the onset of neuronal damage. This can provide additional time for the neurons to try to reestablish homeostasis and proper metabolic functioning; it can also provide additional time for the introduction of additional drug treatments, such as blood clot dissolving agents or drugs that suppress excitotoxic activity mediated by neuronal receptors.

For all of these reasons, disulfiram can help prevent or reduce damage in both the cardiovascular system and in the brain when used to treat hypoxic/ischemic crises such as stroke, heart attack, cardiac arrest, and asphyxiation.

To take advantage of the biochemical and metabolic processes discussed above, rapid-release injectable formulations of disulfiram can also be administered in advance of surgery that requires cardiac arrest or bypass. For example, during various types of cardiac surgery and neurosurgery, the beating of the heart or the supply of oxygenated blood to a specific organ must be stopped for a certain period of time. Although techniques such as reducing the patient's body temperature (hypothermic circulatory arrest) and providing blood flow to the body using a cardiopulmonary bypass (CPB) machine are normally used, such surgical procedures usually inflict some level of damage to the central nervous systems of patients, as manifested by problems such as short-term memory loss or psychological disruptions.

In addition, some patients who undergo heart surgery are subject to a very high risk of stroke. This might be due to the patient's medical condition or history, or it can be caused by the inability of a diseased or injured heart to handle the circulatory load, which can require that a patient be placed on a pumping support known as an LVAD (left ventricular assist device) for some period of time. All LVAD pumps currently in use tend to cause high levels of blood cell hemolysis, and can substantially increase the risk of stroke.

Accordingly, patients undergoing surgery which requires cardiac arrest or a disruption of blood supply to a specific organ, or patients who require artificial pumping support for some period of time, can be administered disulfiram in a rapid-release injectable formulation on an anticipatory basis, to avoid or minimize the damage that could otherwise be caused by adverse events that might be induced by the surgical procedure.

An important aspect of this invention is that disulfiram has already been extensively tested and widely used to treat chronic alcoholism. It has no adverse side effects in most people, and the side effects that occasionally occur in some patients are usually mild if the patient does not also consume alcohol In the words of Banys 1988, "Disulfiram is remarkably safe and well tolerated in the 250 mg per day recommended dosage."

The preferred mode of administration of the injectable formulations described herein, when used to treat stroke, heart attack, cardiac arrest, and other crisis events, involves parenteral injection (preferably intravenous injection) to achieve rapid delivery to the affected organs. To the best of the Applicant's knowledge, the only prior method of injecting disulfiram involves slow-release formulations described in U.S. Pat. No. 4,678,809 (Phillips 1987). Those slow-release formulations release disulfiram into the circulating blood over a span of at least 30 and up to 90 days, which is useful for treating chronic alcoholics who might fail to take disulfiram tablets regularly. Clearly, a slow-release formulation would not be suitable for rapid delivery of disulfiram to reduce the catastrophic damage of a stroke, cardiac arrest, or hemorrhaging aneurysm.

Accordingly, this invention discloses a different type of rapid-release, rapid-diffusion injectable formulation. As used herein, "rapid release" and "rapid diffusion" refer to the release, into circulating blood, of a substantial fraction (such as about 20% or more) of the disulfiram contained in a formulation, within a short span of time (such as an hour or less) after the formulation is injected into the bloodstream.

One preferred embodiment of a rapid-release carrier liquid contains water mixed with a soluble or miscible organic compound that has a plurality of hydroxyl groups, such as propylene glycol, dextran, or a cyclodextrin, in roughly 1:1 proportions. The mixture preferably should also contain a suitable quantity (such as about 5%) of a buffer compound, such as mixture of a carboxylic acid and a salt thereof (such as benzoic acid and sodium benzoate).

Similar carrier liquids are used to inject other hydrophobic compounds, such as diazepam (Valium).

If desired, a rapid-release injection of disulfiram can be supplemented by a slow-release injection and/or oral administration, to maintain desired concentrations over a prolonged period of time.

Various salts or analogs of disulfiram may also be used, provided that (1) they must be pharmaceutically acceptable, and (2) they must be therapeutically effective when used as described herein. In general, a salt or analog can be presumed to have beneficial therapeutic effects if it can chelate iron or copper ions or inhibit the enzymatic activity of xanthine oxidase, which can be determined using in vitro screening tests. Salts or analogs which function in a desirable manner in in vitro screening tests can be tested for physiological acceptability and therapeutic effectiveness using in vivo tests using laboratory animals such as rodents. For example, surgical interventions which temporarily shut off blood supply to the brain or heart of a lab animal are widely used for research involving methods of treating stroke or heart attack, and various convulsant and other drugs are used to cause oxidative or excitotoxic damage in the brain or to model neurodegenerative diseases such as Parkinson's disease. Such procedures and compounds are well known to those skilled in the art, and they can be used to test salts and analogs of disulfiram for therapeutic effectiveness.

Neurodegenerative Diseases

In addition to the use of disulfiram to prevent hypoxic and ischemic damage, it also appears that disulfiram, due to its ability to inhibit oxidative enzymes and chelate metal ions that promote lipid peroxidation, can also reduce some of the damage which occurs in at least some progressive neurodegenerative diseases, such as Parkinson's disease, Alzheimer's disease, Huntington's disease, and ALS. Destructive oxidative processes are believed to be involved in Parkinson's and Alzheimer's disease, and certain other activities such as excitotoxicity (which involves neural overexcitation and excessive neurotransmitter activity), which can be triggered by hypoxic or ischemic conditions, are also believed to occur in Parkinson's and Alzehimer's disease (Sonsalia et al 1989; Tanner 1989; Maragos et al 1987). Since some of the damaging processes involved in hypoxia/ischemia are also implicated in various neurodegenerative diseases, it appears that disulfiram may be useful in helping to reduce or delay the damage caused by at least some progressive neurodegenerative diseases.

In long-term use for purposes such as slowing or preventing the progression and damage of a degenerative disease, oral ingestion of 125 or 250 mg disulfiram tablets or capsules is the preferred method of administration.

Co-administration of Disulfiram with Other Drugs

Another aspect of this invention involves the joint administration of disulfiram and a second active agent which normally is degraded by oxidative enzymes. As an example, various drugs are referred to as NMDA antagonists, since they suppress excitatory activity at the NMDA (N-methyl-D-aspartate) class of receptors on the surfaces of neurons. NMDA antagonists are promising therapeutic agents that can reduce hypoxic and ischemic damage; see, e.g., U.S. Pat. Nos. 4,888,347 (Woodruff et al 1989) and 5,034,400 (Olney 1991). However, at least some NMDA antagonists such as dextromethorphan are rapidly degraded by oxidative enzymes such as cytochrome P-450. By reducing the rate at which other therapeutic drugs such as NMDA antagonists are degraded by oxidative enzymes, disulfiram administered in conjunction with such other drugs can function as an anti-oxidant to sustain desirable concentrations of the other drugs in the blood for longer periods of time, while also exerting its own neuroprotective effects.

Thus there has been shown and described a new method of using disulfiram as a cytoprotective agent. It will be apparent to those skilled in the art that various changes and modifications to the specific embodiments described herein are possible. Such changes that do not depart from the spirit and scope of the invention are deemed to be covered by the invention, which is limited only by the claims that follow.

REFERENCES

Adelman, G. (editor), *Encyclopedia of Neurosciences* (Birkhauser, Boston, 1987)

Banys, P., "The clinical use of disulfiram (Antabuse): A review," *J. Psychoactive Drugs* 20(3): 243–260 (1988)

Cornford, E. M., et al, "Reduction in brain glucose utilization rate after tryptophol treatment," *J. Neurochemistry* 36(5): 1758–1765 (1981)

Jennische, E., and Hansson, H.-A., "Disulfiram is protective against postischemic cell death in the liver," *Acta Physiol, Scanda.* 122: 199–201 (1984)

Krause, G. S., et al, "Brain cell death following ischemia and reperfusion: a proposed biochemical sequence," *Critical Care Medicine* 16(7): 714–726 (1988)

Maragos, W. F., et al, "Glutamate dysfunction in Alzheimer's disease: An hypothesis," *Trends in Neuroscience* 10(2): 65–68 (1987)

Misiorowski, R. L., et al, "Inhibition of lipid peroxidation in spinal cord homogenates by various drugs," *Exper. Neurol.* 81: 714–721 (1983)

Sonsalla, P. K., et al, "Methamphetamine-induced nigrostriatal dopaminergic toxicity," *Science* 243: 398–400 (1989)

Tanner, C. M., "The role of environmental toxins in the etiology of Parkinson's disease," *Trends in Neuroscience* 12(2): 49–54 (1987)

I claim:

1. A method of reducing hypoxic damage to a mammalian brain, comprising the administration to a susceptible mammal of a therapeutically effective quantity of a compound selected from the group consisting of disulfiram, a pharmaceutically acceptable and effective salt of disulfiram which can penetrate a mammalian blood-brain barrier, and a pharmaceutically acceptable and effective analog of disulfiram which can penetrate a mammalian blood-brain barrier.

2. The method of claim 1 wherein the hypoxic damage to the brain is caused by an event selected from the group consisting of stroke, cardiac arrest, asphyxiation, poisoning, hemorrhage, and trauma involving loss of blood.

3. The method of claim 1 wherein the hypoxic damage to the brain is caused by an event relating to a surgical procedure that requires temporary disruption of blood flow to the brain.

4. The method of claim 1 wherein the disulfiram, or said salt or analog thereof, is administered by means of parenteral injection.

5. The method of claim 1 wherein the disulfiram, or said salt or analog thereof, is administered by means of oral ingestion.

6. A method of reducing neurologic damage caused by a progressive neurodegenerative disease, comprising the administration to a susceptible mammal of a therapeutically effective quantity of a compound selected from the group consisting of disulfiram, a pharmaceutically acceptable and effective salt of disulfiram which can penetrate a mammalian blood-brain barrier, and a pharmaceutically acceptable and effective analog of disulfiram which can penetrate a mammalian blood-brain barrier.

7. The method of claim 6 wherein the disulfiram, or said salt or analog thereof, is administered by means of oral ingestion.

8. A method of reducing hypoxic or ischemic neurologic damage, comprising the co-administration to a susceptible mammal of therapeutically effective quantities of a first neuroprotective agent comprising a neuroprotective drug, in conjunction with an anti-oxidant drug selected from the group consisting of:
 a. disulfiram;
 b. a pharmaceutically acceptable and effective salt of disulfiram; and,
 c. a pharmaceutically acceptable and effective analog of disulfiram, wherein the first neuroprotective agent would be rapidly metabolized by oxidative enzymes if administered to the mammal in the absence of disulfiram, and wherein the anti-oxidant drug is administered in a quantity sufficient to significantly inhibit oxidative enzymatic degradation of the first neuroprotective agent.

9. The method of claim 8 wherein the first agent comprises an NMDA antagonist.

* * * * *